United States Patent
Gradtke et al.

(10) Patent No.: US 7,935,701 B2
(45) Date of Patent: May 3, 2011

(54) MICROBICIDAL COMPOSITION BASED ON FORMALDEHYDE DONOR COMPOUNDS AND ANTIOXIDANTS

(75) Inventors: Ralf Gradtke, Tornesch (DE); Wolfgang Beilfuss, Hamburg (DE); Klaus Weber, Hamburg (DE); Wolfgang Siegert, Ellerau (DE)

(73) Assignee: Air Liquide Sante (International), Paris (FR)

( * ) Notice: Subject to any disclaimer, the term of this patent is extended or adjusted under 35 U.S.C. 154(b) by 1371 days.

(21) Appl. No.: 11/444,932

(22) Filed: Jun. 1, 2006

(65) Prior Publication Data

US 2006/0223806 A1   Oct. 5, 2006

Related U.S. Application Data

(62) Division of application No. 10/933,878, filed on Sep. 3, 2004.

(30) Foreign Application Priority Data

Sep. 4, 2003   (DE) .................................. 103 40 830

(51) Int. Cl.
- *A01N 43/66* (2006.01)
- *A01N 43/76* (2006.01)
- *A61K 31/53* (2006.01)
- *A61K 31/42* (2006.01)

(52) U.S. Cl. .......................... 514/241; 514/374; 514/375

(58) Field of Classification Search .................. 514/241, 514/374, 375

See application file for complete search history.

(56) References Cited

U.S. PATENT DOCUMENTS

| 5,221,715 | A * | 6/1993 | Kagawa et al. ............... 525/240 |
| 2001/0021711 | A1 * | 9/2001 | Beilfuss et al. ............... 514/245 |

* cited by examiner

*Primary Examiner* — Yong S Chong
(74) *Attorney, Agent, or Firm* — Young & Thompson

(57) ABSTRACT

Microbicidal composition for product preservation, including a microbicidal composition which comprises a) at least one formaldehyde donor compound and b) at least one antioxidant chosen from gallic esters, phenol derivatives, L-ascorbic acid, and salts and derivatives thereof, and tocopherols and derivatives thereof, and to the use thereof for the preservation of technical products, for example fuels and lubricants.

27 Claims, No Drawings

MICROBICIDAL COMPOSITION BASED ON FORMALDEHYDE DONOR COMPOUNDS AND ANTIOXIDANTS

CROSS REFERENCE TO RELATED APPLICATIONS

This application is a divisional of application Ser. No. 10/933,878, filed on Sep. 3, 2004.

BACKGROUND

The present invention relates to a microbicidal composition and to its use for preserving technical products.

Preservatives are used in many aqueous systems in order to control microbial growth. An important field of use of chemical preservatives is in technical products such as water-mixed cooling lubricants, fuels, paints and coatings. For example, their use in diesel fuels is necessary because microorganisms can multiply therein, particularly when water of condensation settles to the bottom or is present in finely dispersed form within the fuels. If microbial growth is not suppressed it leads to sludge formation (biomass) and to corrosion by metabolic products of the microorganisms (biocorrosion).

It has been known for a relatively long time to use formaldehyde donor compounds as biocides in technical products since they not only have an effect against bacteria, but also against yeasts and moulds. Such formaldehyde donor compounds include, inter alia, O-formals and N-formals.

DE 199 61 621 A1 discloses a stable microbicidal composition for technical products which comprises at least one bactericidal N-formal, at least one fungicide and at least one stabilizer, e.g. 2-mercaptopyridine N-oxide, and corresponding salts.

DE 198 42 116 A1 discloses the use of methylenebisoxazolidine derivatives for increasing the solubility of derivatives of 1H-benzimidazol-2-ylcarbamic acid in liquid preparations or preservatives for use in technical products. The compositions described therein can comprise further active ingredients, in particular N-formals and/or O-formals, additives and/or auxiliaries, e.g. stabilizers.

Further microbicidal compositions which comprise formaldehyde donor compounds as active ingredient are known from U.S. Pat. No. 4,655,815, GB 2 274 779 A, EP 0 327 220 B1, DE 41 41 953 A1, U.S. Pat. Nos. 5,428,050, 5,496,842, DE 197 05 085 A1, DE 197 22 858 A1 and DE 101 22 380 A1.

Furthermore, there are numerous commercially available preservatives based on N-formals and/or O-formals.

One example of the use of N-formals in a commercial product is the reaction product of formaldehyde or paraformaldehyde and ethanolamine (Grotan BK=N,N',N''-tris(hydroxyethyl)hexahydrotriazine), which has been used successfully for years as preservative in the cooling lubricant sector.

A further preservative for technical products, in particular for the cooling lubricant sector is Grotan WS, a 1:1 condensation product of p-formaldehyde and isopropanolamine (N,N',N''-tris(β-hydroxypropyl)hexa-hydrotriazine).

For many years use has also been made of a condensation product of p-formaldehyde and isopropanolamine (weight ratio 3:2, Mar 71 or Grotan OX or GrotaMar 71=N,N'-methylenebis(5-methyloxazolidine) in technical products.

During the storage and the transportation of packs containing formaldehyde donor preparations, the problem often arises that the container loses dimensional stability as the storage time continues and can have a so-called "neck-in". The term "neck-in effect" is understood as meaning the permanent deformation of a container, such as an indentation of the material, shrinkage, deformation of the container ranging to severe deformation or deviation from the dimensional stability. For example, in the case of packs containing Grotan OX, a neck-in effect arises after about 14 days, and at elevated storage temperatures after just 7 to 14 days. For other preparations, such as combinations of Grotan® OX with urea (e.g. Grotan® OF) or fungicides (e.g. Grotan® OD), the onset of the neck-in effect may also arise after a delay, e.g. after 2 to 6 months at ambient temperature. System cleaners such as Grotanol SR 1 may also possibly exhibit a neck-in following storage.

Since the neck-in effect impairs the stackability of packs, the risk of accident during their handling, storage and transportation is increased, which overall reduces the acceptance by the consumer or customer. Moreover, a final product which, under transportation conditions (e.g. sea transportation in tropical countries), has a tendency toward deformation of the packaging material and thus represents a safety problem, may require higher insurance premiums. A product not packaged in accordance with requirements is also associated with a reduction in value.

In order to reduce the neck-in effect, it is possible, for example, to use packs with comparatively high wall strengths or more resistant packaging materials. However, this leads to an increase in the costs as a result of the greater material use and expenditure in choosing suitable packagings.

Recently, preservatives, e.g. Grotan® OF, have come onto the market which comprise emission-reducing additives, e.g. urea and urea derivatives, in addition to N-formals. By adding such emission-reducing additives it was possible not only to reduce the emission of the readily volatile formaldehyde from these products, but also to achieve advances in reducing the neck-in effect of formulated products.

However, for some applications, a significant increase in the solids content in the formaldehyde donor preparation as a consequence of incorporating further additives is undesired. For example, in the case of the use of formaldehyde donor preparations as fuel additive, it may lead to the blockage of injection nozzles or deposits in the engine compartment, when, for example, amounts of urea with an emission-reducing effect are used in addition to microbicidal active ingredients.

There thus continues to be a need for preservatives based on formaldehyde donor compounds which contribute, in the form of the formulated product, to a reduction in the neck-in effect on the packs used for storage and for transportation.

SUMMARY

The present invention provides a microbicidal composition based on formaldehyde donor compounds which reduce the problem of the neck-in effect during handling, storage, and transportation of the composition, as a formulated final product, and at the same time, is suitable for applications in which a low solids content in the application preparation is desired.

This object is achieved by the microbicidal composition which comprises
 a) at least one formaldehyde donor compound and
 b) at least one antioxidant chosen from gallic esters, phenol derivatives, L-ascorbic acid, and salts and derivatives thereof, and tocopherols and derivatives thereof.

Surprisingly, it has been found that the microbicidal composition according to the invention and based on formaldehyde donor compounds and selected antioxidants in the form of a final product packaged in packs leads to a significantly reduced neck-in effect than compositions known to date which are prepared on the basis of formaldehyde donor compounds alone (e.g. Grotan® OX). Furthermore, even the addition of small amounts of antioxidant relative to the formaldehyde donor compound are enough to reduce the neck-in effect. This is advantageous particularly when the microbicidal composition is used in fuels, in particular in diesel fuels, because a significantly higher solid content there may lead to blockages of injection nozzles and deposits in the engine compartment.

DESCRIPTION OF PREFERRED EMBODIMENTS

The present invention includes the microbicidal composition which comprises
  a) at least one formaldehyde donor compound and
  b) at least one antioxidant chosen from gallic esters, phenol derivatives, L-ascorbic acid, and salts and derivatives thereof, and tocopherols and derivatives thereof.

Surprisingly, it has been found that the microbicidal composition according to the invention and based on formaldehyde donor compounds and selected antioxidants in the form of a final product packaged in packs leads to a significantly reduced neck-in effect than compositions known to date which are prepared on the basis of formaldehyde donor compounds alone (e.g. Grotan® OX). Furthermore, even the addition of small amounts of antioxidant relative to the formaldehyde donor compound are enough to reduce the neck-in effect. This is advantageous particularly when the microbicidal composition is used in fuels, in particular in diesel fuels, because a significantly higher solid content there may lead to blockages of injection nozzles and deposits in the engine compartment.

The microbicidal composition according to the invention comprises, as component a), at least one formaldehyde donor compound. Preferred formaldehyde donor compounds, which are also referred to as formaldehyde eliminators, are formals. The term "formals" is a collective term for acetals of formaldehyde. The formal used here is preferably an N-formal and/or O-formal. N-formals are reaction products or condensation products of an amine or amide function and a formaldehyde-supplying compound. N-formals are, in particular, reaction products or condensation products of a mono- or polyhydric, amino-substituted $C_1$- to $C_{10}$-alkyl, -aryl, -aralkyl alcohol and a formaldehyde-supplying compound. O-formals are reaction products of a mono- or polyhydric $C_1$- to $C_{10}$-alkyl, -aryl, -aralkyl alcohol or a glycol or glycol ether and a formaldehyde-supplying compound.

Examples of O-formals which can be used in the microbicidal composition according to the invention are (ethylenedioxy)dimethanol, benzyl alcohol hemiformal, propylene glycol hemiformal and butyl diglycol hemiformal.

Suitable N-formals are urea-formaldehyde adducts, such as 1,3-bis(hydroxymethyl)urea, tetrahydro-1,3,4,6-tetrakis{hydroxymethyl}imidazole[4,5-d]imidazole-2,5{1H,3H}-dione (Protectol 140), N,N"-methylenebis[N'-[3-hydroxymethyl)-2,5-dioxoimidazolidin-4-yl]urea] (imidazolidinylurea), 1-[1,3-bis(hydroxymethyl)-2,5-dioxoimidazolidin-4-yl]-1,3-bis(hydroxymethyl)urea (diazolidinylurea), 1,3-bis(hydroxymethyl)-5,5-dimethylimidazolidine-2,4-dione (DMDMH), amino acid derivatives, such as N-hydroxymethylglycine or salts, N,N',N"-tris(hydroxyethyl)hexahydrotriazine, N,N',N"-tris(β-hydroxypropyl)hexahydrotriazine, N-methylolchloroacetamide, cis-isomer of 1-(3-chloroallyl)-3,5,7-triaza-1-azonia-adamantane chloride, 1-(3-chloroallyl)-3,5,7-triaza-1-azonia-adamantane chloride, 5-(polyoxymethylene)-1-aza-3,7-dioxabicyclo[3.3.0]octane, ({[1-methyl-2-(5-methyloxazolidin-3-yl)ethoxy]methoxy}methoxy)methanol, 4,4-dimethyloxazolidine, 7a-ethyl-dihydro-1H,3H,5H-oxazolo[3,4-c]oxazole, 2-(hydroxymethylamino)ethanol, 1-(hydroxymethylamino)-2-propanol and N,N'-methylenebis(5-methyloxazolidine). Particularly preferred N-formals are chosen from N,N',N"-tris(hydroxyethyl)hexahydrotriazine, N,N',N"-tris(β-hydroxypropyl)hexahydrotriazine and N,N'-methylenebis(5-methyloxazolidine). N,N'-methylenebis(5-methyloxazolidine) is most preferred.

The microbicidal composition according to the invention comprises, as component b), at least one antioxidant chosen from gallic esters, phenol derivatives, L-ascorbic acid, and salts and derivatives thereof, and tocopherols and derivatives thereof.

In one preferred embodiment, the gallic ester used as antioxidant is an alkyl gallate with a branched or unbranched, substituted or unsubstituted $C_1$- to $C_{20}$-alkyl group, in particular $C_2$- to $C_{16}$-alkyl group and most preferably $C_6$- to $C_{14}$-alkyl group. Preferred alkyl gallates are chosen from methyl gallate, ethyl gallate, 2-hydroxyethyl gallate, propyl gallate, isopropyl gallate, butyl gallate, isobutyl gallate, tert-butyl gallate, isopentyl gallate, octyl gallate, isooctyl gallate, nonyl gallate, decyl gallate, dodecyl gallate, ethylhexyl gallate, tetradecyl gallate, hexadecyl gallate and octadecyl gallate. It is particularly preferred to use octyl gallate and/or dodecyl gallate as alkyl gallate in the microbicidal composition according to the invention. Dodecyl gallate (also referred to below as lauryl gallate) is most preferred.

If a phenol derivative is used as component b), it is preferably chosen from 2,6-di-tert-butyl-p-cresol, 2-tert-butyl-4-methylphenol, 2-tert-butyl-5-methylphenol and 3-tert-butyl-4-hydroxyanisole (BHA). The most preferred phenol derivative is 2,6-di-tert-butyl-p-cresol.

Further compounds which can be used as antioxidant include L-ascorbic acid (vitamin C), and salts and derivatives thereof. Preferred derivatives of L-ascorbic acid are their fatty acid esters, in particular 6-O-palmitoyl-L-ascorbic acid.

Furthermore, component b) can be chosen from tocopherols (in particular α-tocopherol) and derivatives thereof (in particular esters of tocopherols, such as acetates, linoleates, nicotinates and succinates and more preferably esters of α-tocopherol, such as, for example, α-tocopherol acetate, α-tocopherol linoleate, α-tocopherol nicotinate and α-tocopherol succinate). Although the tocopherols used may be of synthetic origin, tocopherols of natural origin may be used. It is possible to use sterically uniform enantiomers or enantiomer mixtures of tocopherols, and accordingly for the derivatization to acetate, succinate, linoleate or nicotinate, it is possible to use tocopherols of natural and/or synthetic origin and sterically uniform enantiomers or mixtures of tocopherols (in particular α-tocopherol).

Preference is also given to antioxidants which are approved under foodstuffs legislation, such as ascorbic acid and salts thereof, 6-palmitoyl-L-ascorbic acid, 2,6-di-tert-butyl-p-cresol (BHT), 3-tert-butyl-4-hydroxy-anisole (BHA), α-tocopherol and derivatives thereof, propyl, octyl, dodecyl gallate (for which there is, for example, a toxicological assessment), and liquid antioxidants, such as α-tocopherol or α-tocopherol acetate. Liquid antioxidants in particular offer advantages during handling, dosing and incorporation into the preservatives (e.g. due to higher dissolution rate). Furthermore, for some applications of preservatives, such as the use as fuel additive, solid antioxidants are less preferable because solid residues can lead to blockage of injection nozzles and to deposits on the injection nozzles and in the engine compartment.

Further examples of antioxidants which can be incorporated as component b) into microbicidal compositions according to the invention are given in *International Cosmetic Dictionary and Handbook*, 8th edition, volume 2, p. 1727. Experts are able to choose suitable antioxidants based on the present invention and to optimize them with regard to their use concentration in order to prevent the neck-in effect which is caused on packs of formulated formaldehyde donor preparations.

In a preferred embodiment, the weight ratio of formaldehyde donor compound to antioxidant a):b) is in the range from 99.9999:0.0001 to 90:10, more preferably from 99.999:0.001 to 99:1 and in particular from 99.99:0.01 to 99.5:0.5

One advantage of the invention thus lies in the fact that only a small amount of antioxidant is required in order to achieve a reduction in the neck-in effect with formulated final products.

The microbicidal composition according to the invention can be in the form of a powder, a homogeneous liquid (e.g. a solution), a dispersion or a paste, where it is preferably flowable.

A preferred embodiment of the invention relates to a microbicidal composition which is in the form of a solution. Consequently, as well as the active ingredient component a) and the antioxidant b), the microbicidal composition according to the invention comprises solvent and/or solubility promoter as further component c). The solvent and/or the solubility promoter are preferably chosen from water, alcohols, glycols, polyols or derivatives, such as ethers or esters and aliphatic and/or aromatic hydrocarbons. Water is most preferred.

In addition, the microbicidal composition according to the invention can comprise, as optional component d) one or more further biocides (e.g. Pyrion-Na, Kathon 893, benzisothiazolone, etc.) and/or one or more additives, for example corrosion inhibitors, alkalizing agents, dyes, perfume, viscosity-modifying agents, foam inhibitors, emulsifiers, stabilizers, dispersants, complexing agents, etching agents, cleaning components, surfactants, pigments, essential oils, odor-modifying additives, lubricant additives, care additives, fillers and polymers.

In a further preferred embodiment, an emission-reducing additive which is chosen from urea, urea derivatives, amino acids, guanidine and guanidine derivatives is excluded from the microbicidal composition according to the invention.

In addition, it is preferred that components a) to d) are present in the following amounts in the microbicidal composition according to the invention (where the percentages by weight given in each case refer to the weight of the total composition):
 a) 0.005 to 99.9999% by weight (preferably 1 to 99.999% by weight and in particular 5 to 99.99% by weight,
 b) 0.0001 to 10% by weight (preferably 0.001 to 1% by weight and in particular 0.01 to 0.5% by weight),
 c) 0 to 99.995% by weight (preferably 0 to 10% by weight and in particular 0 to 1% by weight) and
 d) 0 to 50% by weight (preferably 0 to 30% by weight and in particular 0 to 20% by weight).

In a further embodiment of the invention, the microbicidal composition according to the invention is in the form of a concentrate, i.e. it comprises comparatively large amounts of components a), b) and optionally d). In this connection, it is preferred that the amount of solvent and/or solubility promoter (preferably water) in the composition according to the invention is 10% by weight or less, preferably 5% by weight or less and in particular 1% by weight or less. Most preference is given to composition which is free from any solvent and/or solubility promoter, and by far the most preferred is free from water.

Preference is also given to microbicidal compositions which comprise the following components in the quantitative amounts given (in each case based on the weight of the total composition):
 a) 90 to 99.9999% by weight, in particular 99 to 99.999% by weight and most preferably 99.90 to 99.995% by weight, of N,N'-methylenebis(5-methyloxazolidine) (Grotan® OX) and
 b) 0.0001 to 10% by weight, in particular 0.001 to 1% by weight and most preferably 0.005 to 0.01% by weight, of dodecyl gallate;
 a) 90 to 99.9999% by weight, in particular 99 to 99.999% by weight and most preferably 99.90 to 99.995% by weight, of N,N'-methylenebis(5-methyloxazolidine) (Grotane®OX) and
 b) 0.0001 to 10% by weight, in particular 0.001 to 1% by weight and most preferably 0.005 to 0.01% by weight, of 2,6-di-tert-butyl-p-cresol.

According to the invention, the microbicidal composition can consist merely of the abovementioned components a) and b) in the given quantitative amounts.

The microbicidal composition according to the invention is prepared by simply mixing component a) with component b) and optionally further constituents, such as solvent and/or solubility promoter, and further biocides or additives (components c) and d)).

In addition, the invention relates to the use of the microbicidal composition according to the invention for preserving technical products. Examples of technical products are cooling lubricants, cooling lubricant concentrates, fuels (in particular diesel fuels), lubricants, coatings, paints, technical dispersions or emulsions or disinfectant cleaners for production plants (so-called system cleaners such as, for example, Grotanol® SR 1). The microbicidal composition according to the invention can, however, generally be used in all fields of use where the microbial attack by bacteria, fungi, algae, yeasts and/or viruses exert a troublesome influence.

As well as the excellent activity spectrum against microbial attack suitable primarily for technical products, the microbicidal composition according to the invention offers the advantage that the problem of the neck-in effect, which arises in the case of formaldehyde donor preparations, in the packs of formulated final products can be significantly reduced through the presence of just small amounts of selected antioxidants. As a result of the reduced deformation of the packaging material of the final products, the risk of accident which arises due to impairment of the stackability of the deformed packs can be reduced, as a result of which acceptance by the consumer or customer increases. Furthermore, it is not necessary to choose more suitable packaging materials or to use packs with higher wall strength, but it is possible to fall back on the commercially available or favorable materials, which leads to a cost saving.

In further embodiments, the microbicidal composition according to the invention is used
 for reducing the susceptibility to oxidation,
 for reducing discolorations,
 for reducing deposits and gum formation (the latter being understood as meaning a resinification, which includes the formation of dark, sparingly soluble to insoluble resin-like masses which reduce yields, e.g. during combustion, and disturb processes, and hinder cleaning),
 for improving the low-temperature stability and flowability and for prolonging the shelf-life of technical products. Suitable technical products for this are those mentioned above. The mentioned uses, however, are primarily of importance for use of the microbicidal composition according to the invention in fuels, in particular diesel fuels, and in lubricants. In these fields of use, the composition according to the invention can also serve to reduce deposits on injection nozzles in engines, of blockages of the same and of deposits in engines.

In addition, the present invention relates to a method of reducing the deformation of a packaging with a preparation enclosed therein which comprises a) at least one formaldehyde donor compound and b) at least one antioxidant, where the at least one antioxidant is chosen from gallic esters, phenol derivatives, L-ascorbic acid, and salts and derivatives thereof, and tocopherols and derivatives thereof.

In this connection, the expression "reduction of deformation" includes not only a reduction in the extent of a deformation, but also complete nonappearance, and time-delayed appearance of a deformation.

The term "deformation" describes in particular the so-called neck-in effect, which is understood as meaning the permanent deformation of a container in the sense of an indentation of the packaging material, a shrinkage, a deformation of the container ranging to severe deformation or deviation from the dimensional stability. During the storage and the transportation of packs with formaldehyde donor preparations enclosed therein, in particular on the basis of N-formals (e.g. Grotan® OX), such a neck-in effect was observed at room temperature after just about 14 days. At higher storage temperatures, a visible neck-in effect can arise after just 7 to 14 days. By adding the selected antioxidants, the neck-in effect during storage or transportation of the packaging with the preparation enclosed therein is reduced.

The packaging in which the preparation is enclosed is a plastic bottle, a plastic container, a metal container, a plastic-coated metal container or a container made of composite film. Here, said packagings may either be small packs or large packs.

In a preferred embodiment, the preparation enclosed in the packaging is the microbicidal composition according to the invention. Thus, the preferred formaldehyde donor compounds, antioxidants, solvents and solubility promoters, further microbiocides, additives, etc. used are the compounds already described above.

The invention is explained in more detail by reference to the following examples. Unless stated otherwise, all of the percentages are based on the weight.

EXAMPLES

Example 1

Microbicidal compositions according to the invention were prepared which consisted of 99.9% by weight of Grotan® OX (N,N'-methylenebis(5-methyloxazolidine)) and of in each case 0.1% by weight of various antioxidants (compositions B to F). The comparison used was composition A, which consisted only of formaldehyde donor compound (100% by weight of Grotan® OX).

To prepare these compositions, Grotan OX was initially introduced, and the antioxidants were added with stirring (about 30 minutes at room temperature). The appearance of each freshly prepared composition was checked. Afterwards, 100 g of the particular preparation were placed into white sample bottles (250 ml), the bottles were closed and stored at room temperature (20 to 25° C.) in the air-conditioned laboratory on a laboratory bench. The sample bottles used were a white unprinted 250 ml plastic bottle (polyethylene PE-HD, Hoechst, Hostalen GF 4750; Schülke & Mayr 13048). The appearance of the sample bottle stored in this way was checked after a storage period of 33 days, 4 months, 10 months and 3 weeks, and 1 year. After 1 year, the appearance and the Hazen color number of the stored compositions was also checked. The results of these investigations are summarized in Table I.

TABLE I

Storage of microbicidal compositions according to the invention in 250 ml sample bottles (white) at room temperature

|  | A | B | C | D | E | F |
|---|---|---|---|---|---|---|
| Lauryl gallate, 97% strength (Aldrich) |  | 0.1 |  |  |  |  |
| L(+)-ascorbic acid (Merck) |  |  | 0.1 |  |  |  |
| 6-O-palmitoyl-L-ascorbic acid (Fluka) |  |  |  | 0.1 |  |  |
| 2,6-di-tert-butyl-p-cresol (Fluka) |  |  |  |  | 0.1 |  |
| DL-α-tocopherol (Merck) |  |  |  |  |  | 0.1 |
| Grotan OX | 100.0 | 99.9 | 99.9 | 99.9 | 99.9 | 99.9 |
| Appearance of the composition (freshly prepared) | clear colorless | clear colorless | clear colorless | clear colorless | clear colorless | clear colorless |
| Appearance of the bottle (after 33 days) | unchanged | unchanged | unchanged | unchanged | unchanged | unchanged |
| Appearance of the bottle (after 4 months) | considerable neck-in | unchanged | unchanged | unchanged | unchanged | slight neck-in |
| Appearance of the bottle after 10 months and 3 weeks | considerable neck-in | unchanged | considerable neck-in | considerable neck-in | unchanged | considerable neck-in |
| Appearance of the composition (after 1 year) | clear colorless | clear colorless | clear slightly yellow | clear colorless | clear colorless | clear colorless |
| Hazen color number of the composition (after 1 year) | 7 | 78 | 45 | 32 | 5 | 120 |
| Appearance of the bottle (after 1 year) | considerable neck-in | unchanged | considerable neck-in | considerable neck-in | unchanged | considerable neck-in |

It is clear from Table I that the microbicidal compositions B to F, into which an antioxidant within the meaning of the invention is incorporated, have a significantly reduced neck-in effect when stored in sample bottles compared with comparison composition A (without antioxidant). In particular, in the case of the compositions B and E according to the invention, which consisted of 99.9% by weight of Grotan® OX and 0.1% by weight of lauryl gallate or 2,6-di-tert-butyl-p-cresol, respectively, no neck-in effect arose even after 1 year (the appearance of the sample bottles was unchanged). Also in the case of compositions C (with 0.1% by weight of L(+)-ascorbic acid), D (with 0.1% by weight of 6-O-palmitoyl-L-ascorbic acid) and F (with 0.1% by weight of DL-α-tocopherol), it was possible to establish improvements in the appearance of the bottle compared with comparison composition A (without antioxidant). Thus, in the case of these compositions a considerable neck-in effect was evident only in the test after a storage period of 10 months and 3 weeks, whereas this effect was established for comparison composition A after just 4 months. Overall, thus, the presence of small amounts of selected antioxidants in preservatives based on N-formals, such as N,N'-methylenebis(5-methyloxazolidine), can achieve a significant reduction in the neck-in effect.

Example 2

Microbicidal compositions according to the invention were prepared in which, as the main constituent, Grotan® OX and, as antioxidant, either lauryl gallate (compositions B to F) or 2,6-di-tert-butyl-p-cresol (compositions G to K) were in each case incorporated in varying amounts. As comparison, composition A was tested which consisted only of formaldehyde donor compound without antioxidant (100% by weight of Grotan® OX). The compositions were prepared as described in Example 1 and the appearance of the freshly prepared compositions was checked. Afterwards, 100 g of the particular compositions were placed into 100 ml plastic sample bottles (blue, polyethylene PE-HD, Lupolen 4261 A, BASF; Schülke & Mayr 18024), the respective bottles were closed and then stored, one experimental series being carried out at 25° C. (room temperature, RT), and a further being carried out at 40° C., in each case in an air-conditioned room. The appearance of the sample bottles stored in this way was checked for both experimental series and after 34 days, 14 weeks and 6 months. The results of these investigations are summarized in Table II.

It is clear from Table II that a very good reduction in the neck-in effect is achieved with the antioxidant lauryl gallate even in a small amount based on the total composition, namely of 0.005% by weight. After a storage time of 6 months, a neck-in effect was found neither at room temperature nor at increased temperature (40° C.). In the case of compositions G to K, into which 2,6-di-tert-butyl-p-cresol have been incorporated in varying amounts, the amount required to prevent the neck-in effect is somewhat higher, although the neck-in effect can be suppressed at least over relatively short periods even with low concentrations of this antioxidant.

Example 3

Microbicidal compositions were prepared in which, as the main component, Grotan® OX and, as the antioxidant, small amounts of lauryl gallate (compositions A to G) were incorporated. The comparison used was composition H which consisted of 100% by weight of Grotan® OX. The amount of lauryl gallate used was in the range from 0.00015% by weight (composition G) to 0.01% by weight (composition A). The compositions were prepared as described in Example 1 and the appearance of the freshly prepared compositions was checked. Afterwards, 100 g of the particular compositions were placed into 100 ml plastic sample bottles (blue, polyethylene PE-HD, Lupolen 4261 A, BASF; Schülke & Mayr 18024), the respective sample bottle was closed and subsequently stored at 40° C. in an air-conditioned room. The appearance of the stored sample bottles was checked after 4 weeks, 6 weeks, 2, 3 and 6 months. The results of these investigations are summarized in Table III.

TABLE II

Storage of microbicidal compositions according to the invention in 100 ml sample bottles (blue) at room temperature (RT) and 40° C.

| | A | B | C | D | E | F | G | H | I | J | K |
|---|---|---|---|---|---|---|---|---|---|---|---|
| Lauryl gallate, 97% strength (Aldrich) | | 0.10 | 0.05 | 0.02 | 0.01 | 0.005 | | | | | |
| 2,6-di-tert-butyl-p-cresol (Fluka) | | | | | | | 0.10 | 0.05 | 0.02 | 0.01 | 0.005 |
| Grotan OX | 100.0 | 99.90 | 99.95 | 99.98 | 99.99 | 99.995 | 99.90 | 99.95 | 99.98 | 99.99 | 99.995 |
| Appearance of the composition (freshly prepared) | clear colorless | clear colorless | clear colorless | clear colorless | clear colorless | clear colorless | clear colorless | clear colorless | clear colorless | clear colorless | clear colorless |
| Appearance of the bottle after 34 days at RT | without change | without change | without change | without change | without change | without change | without change | without change | without change | without change | without change |
| Appearance of the bottle after 34 days at 40° C. | neck-in | without change | without change | without change | without change | without change | without change | without change | without change | without change | neck-in |
| Appearance of the bottle after 14 weeks at RT | neck-in | without change | without change | without change | without change | without change | without change | without change | without change | neck-in | neck-in |
| Appearance of the bottle after 14 weeks at 40° C. | neck-in | without change | without change | without change | without change | without change | without change | without change | without change | neck-in | neck-in |
| Appearance of the bottle after 6 months at RT | considerable neck-in | without change | without change | without change | without change | without change | without change | without change | without change | considerable neck-in | considerable neck-in |
| Appearance of the bottle after 6 months at 40° C. | considerable neck-in | without change | without change | without change | without change | without change | without change | without change | without change | considerable neck-in | considerable neck-in |

TABLE III

Storage of microbicidal compositions according to the invention with varying amounts of lauryl gallate at 40° C.

| | A | B | C | D | E | F | G | H |
|---|---|---|---|---|---|---|---|---|
| Lauryl gallate (Merck) | 0.01 | 0.005 | 0.0025 | 0.0012 | 0.00006 | 0.0003 | 0.000015 | 0.0 |
| Grotan OX | 99.9 | 99.995 | 99.9975 | 99.9988 | 99.9994 | 99.9997 | 99.99985 | 100.0 |
| Appearance of the composition (freshly prepared) | clear colorless | clear colorless | clear colorless | clear colorless | clear colorless | clear colorless | clear colorless | clear colorless |
| Appearance of the bottle after 4 weeks | unchanged | unchanged | unchanged | unchanged | unchanged | unchanged | unchanged | unchanged |
| Appearance of the bottle after 6 weeks | unchanged | unchanged | unchanged | unchanged | unchanged | slight neck-in | slight neck-in | slight neck-in |
| Appearance of the bottle after 2 months | unchanged | unchanged | unchanged | unchanged | unchanged | neck-in | neck-in | neck-in |
| Appearance of the bottle after 3 months | unchanged | unchanged | unchanged | unchanged | very slight neck-in | neck-in | neck-in | neck-in |
| Appearance of the bottle after 6 months | unchanged | unchanged | unchanged | unchanged | neck-in | neck-in | neck-in | neck-in |
| ppm (antioxidant) | 100 ppm | 50 ppm | 25 ppm | 12 ppm | 6 ppm | 3 ppm | 1.5 ppm | 0 ppm |

These investigations show that a certain minimum amount of antioxidant, e.g. lauryl gallate, based on the formaldehyde donor compound, e.g. N,N'-methylenebis(5-methyloxazolidine), must be incorporated into the composition according to the invention in order to avoid the neck-in effect in packs. In the present experimental series, it is found that even a small amount of 0.0012% by weight (12 ppm) of lauryl gallate is suitable, such that no neck-in effect on the plastic bottle used arises after an observation period of 6 months at a temperature of 40° C.

Test Methods:

The Hazen color number (DIN-ISO 6271, also known as "APHA method" or "Platinum-cobalt scale") is defined as mg of platinum per 1 l of solution. For the Hazen stock solution, 1.246 g of potassium hexachloroplatinate(IV) and 1.00 g of cobalt(II) chloride are dissolved in 100 ml of hydrochloric acid and made up to 1 000 ml with distilled water. The Hazen color scale is used to assess the color of virtually water-clear products. It is more narrowly classified in the pale yellowish range than the iodine color scale and extends to water-clear products. The composition in each case was placed into a cell and then the color number was measured using a LICO® 200 color measurement device (Dr Lange GmbH, Berlin).

The appearance of the sample bottles and of any neck-in effect which arose was checked visually and in some cases documented photographically. A slight neck-in is understood as meaning a perceptible to slight indentation of the round containers. Neck-in is understood as meaning a clearly visible indentation of the round containers, with no or only minimal inclination of the vertical axis of the pack. Considerable neck-in is understood as meaning significant deformation of the round containers (on one or more sides), where the vertical axis of the pack is markedly inclined and stacking of the packs is no longer possible.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A microbicidal composition comprising:
   a) N,N'-methylenebis(5-methyloxazolidine); and
   b) 2,6-di-tert-butyl-p-cresol in an amount of about 0.02% to about 0.10%.

2. The composition of claim 1, further comprising an O-formal.

3. The composition of claim 1, further comprising at least one member selected from the group consisting of:
   a) N,N',N"-tris(hydroxyethyl)hexahydrotriazine; and
   b) N, N',N"-tris(β-hydroxypropyl)hexahydrotriazine.

4. The composition of claim 1, further comprising a phenol derivative selected from the group consisting of:
   a) 2-tert-butyl-4-methylphenol;
   b) 2-tert-butyl-5-methylphenol; and
   c) 3-tert-butyl-4-hydroxyanisole.

5. The composition of claim 1, wherein the weight ratio of said N,N'-methylenebis(5-methyloxazolidine) to said 2,6-di-tert-butyl-p-cresol is in the range from about 99.9999:0.0001 to about 90:10.

6. The composition of claim 5, wherein said range is about 99.999:0.001 to about 99:1.

7. The composition of claim 6, wherein said range is about 99.99:0.01 to about 99.5:0.5.

8. The composition of claim 1, wherein said composition further comprises:
   a) at least one solvent or solubility promoter; and
   b) an additive, wherein said additive comprises at least one member selected from the group consisting of:
      1) corrosion inhibitors;
      2) alkalizing agents;
      3) dyes;
      4) perfumes;
      5) viscosity-modifying agents;
      6) foam inhibitors;
      7) emulsifiers;
      8) stabilizers; and
      9) a biocide.

9. The composition of claim 1, wherein said composition comprises said N,N'-methylenebis(5-methyloxazolidine) in the amount of about 0.005% to about 99.9999% of total composition weight.

10. The composition of claim 9, wherein said amount is about 1% to about 99.999% of total composition weight.

11. The composition of claim 10, wherein said amount is about 5% to about 99.99% of total composition weight.

12. The composition of claim 8, wherein said composition comprises said solvent or solubility promoter in the amount of about 0% to about 99.995% of total composition weight.

13. The composition of claim 12, wherein said amount is about 0% to about 10% of total composition weight.

14. The composition of claim 13, wherein said amount is about 0% to about 1% of total composition weight.

15. The composition of claim 8, wherein said composition comprises said additive in the amount of about 0% to about 50% of total composition weight.

16. The composition of claim 15, wherein said amount is about 0% to about 30% of total composition weight.

17. The composition of claim 16, wherein said amount is about 0% to about 20% of total composition weight.

18. The composition of claim 12, wherein said solvent comprises water in the amount of less than about 10% of total composition weight.

19. The composition of claim 18, wherein said amount is less than about 5% of total composition weight.

20. The composition of claim 19, wherein said amount is less than about 1%.

21. The composition of claim 20, wherein said amount is about 0%.

22. The composition of claim 18, wherein said composition comprises N,N'-methylenebis(5-methyloxazolidine) in the amount of about 90% to about 99.9999% of total composition weight.

23. The composition of claim 22, wherein said amount is about 99% to about 99.999% of total composition weight.

24. The composition of claim 23, wherein said amount is about 99.90% to about 99.995% of total composition weight.

25. The composition of claim 18, wherein said composition comprises N,N'-methylenebis(5-methyloxazolidine) in the amount of about 90% to about 99.9999% of total composition weight.

26. The composition of claim 25, wherein said amount is about 99% to about 99.999% of total composition weight.

27. The composition of claim 26, wherein said amount is about 99.90% to about 99.995% of total composition weight.

* * * * *